United States Patent [19]

Karami et al.

[11] Patent Number: 5,263,948

[45] Date of Patent: Nov. 23, 1993

[54] BREATHABLE DISPOSABLE DIAPERS

[75] Inventors: Hamzeh Karami, Mansfield; Ronald E. Vitaris, Worcester, both of Mass.

[73] Assignee: The Kendall Company

[21] Appl. No.: 406,020

[22] Filed: Sep. 12, 1989

[51] Int. Cl.$^5$ .............................................. A61F 13/15
[52] U.S. Cl. .................................. 604/383; 604/358; 604/385.1
[58] Field of Search ...................... 604/369, 370, 385.1, 604/386, 358

[56] References Cited

U.S. PATENT DOCUMENTS

| | | | |
|---|---|---|---|
| 4,360,022 | 11/1982 | Usami et al. | 604/385.1 |
| 4,480,000 | 10/1984 | Watanabe et al. | 604/370 |
| 4,496,360 | 1/1985 | Joffe et al. | 604/385.1 |
| 4,699,620 | 10/1987 | Bernardin | 604/385.1 |
| 4,822,435 | 4/1989 | Igaue et al. | 604/358 |
| 4,887,602 | 12/1989 | O'Leary | 604/385.1 |

FOREIGN PATENT DOCUMENTS

| | | | |
|---|---|---|---|
| 691136 | 5/1940 | Fed. Rep. of Germany | 604/358 |
| 2349168 | 9/1973 | Fed. Rep. of Germany | 604/385.1 |
| 3343622 | 6/1985 | Fed. Rep. of Germany | 604/358 |
| 2515029 | 10/1981 | France | 604/358 |

Primary Examiner—David Isabella
Assistant Examiner—Rob Clarke
Attorney, Agent, or Firm—Alvin Isaacs

[57] ABSTRACT

Novel breathable disposable diapers of per se known configuration comprising a back sheet having a crotch portion and corner portions or wings adapted for engaging the waist and stomach of the wearer, the corner portions being both air-and liquid-permeable, the crotch portion of the back sheet comprising a a liquid-impermeable sheet material carrying an absorbent pad for receiving and retaining body waste materials with the side edges of the sheet material extending around and over the side edges of the pad, whereby to provide a barrier preventing the waste material from escaping through the back of the diaper or through the side edges of the pad.

Preferably, a permeable cover or front sheet, is also provided, the absorbent pad in the crotch portion being sandwiched between the cover and liquid-impermeable sheets.

13 Claims, 1 Drawing Sheet

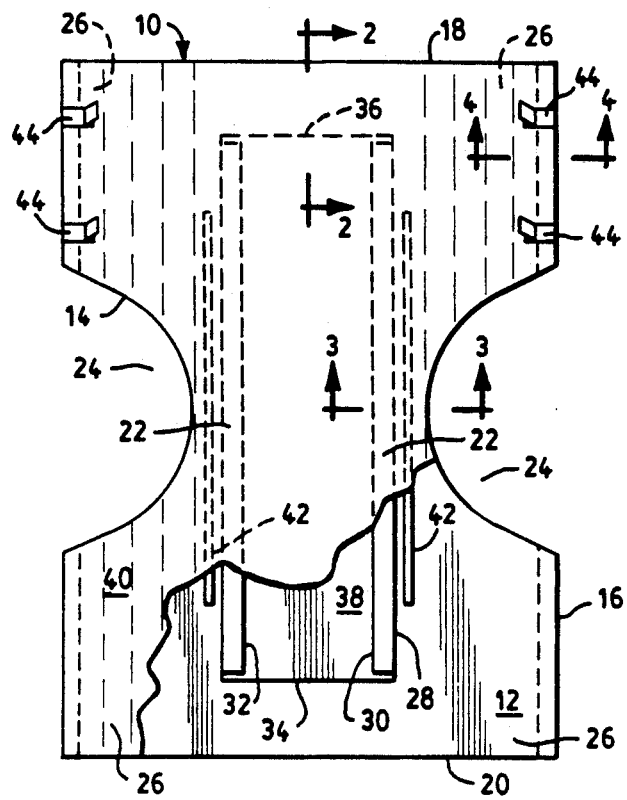
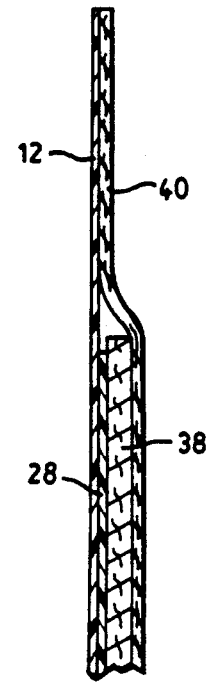
FIG. 1
FIG. 2
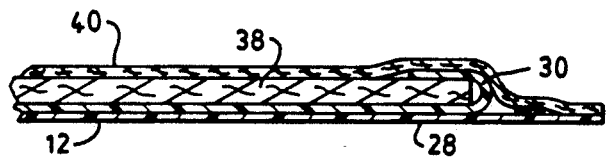
FIG. 3
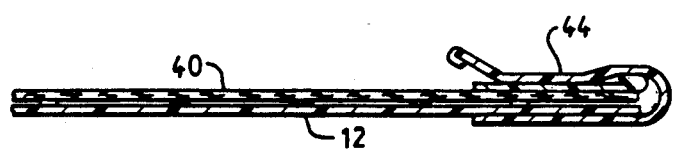
FIG. 4

BREATHABLE DISPOSABLE DIAPERS

BACKGROUND OF THE INVENTION

Disposable diapers for infants and incontinent older people are a major industry and as such constitute a crowded art, competitively speaking.

In general, they comprise a liquid-impermeable back sheet and an absorbent pad assembly comprising at least an absorbent pad in the crotch portion and typically also a liquid-permeable cover or front sheet.

While the back sheet must be liquid-impermeable to prevent escape of body waste materials through the back of the diaper, the prior art, as exemplified by the patent literature, has recognized the advisability that it also be breathable for the comfort of the wearer, particularly in warm weather.

In general, the patent literature has taught that this breathability can be obtained in one of two ways: (1) providing a backsheet consisting of a single sheet material which is both breathable and liquid-impermeable; and (2) employing for the back sheet what is in fact two separate films or sheet materials to provide the combination of breathability and liquid-impermeability.

Illustrative of the former are U.S. Pat. No. 3,156,242 of Crowe teaching the concept of employing a microporous film to provide a breathable backsheet; and U.S. Pat. No. 3,989,867 which discloses a breathable backsheet having tapered hollowed bosses which prevent the passage of liquids while permitting vapors to pass therethrough.

As an illustration of the latter, mention may be made of U.S. Pat. No. 4,341,216 issued to Obenour which teaches a two-element breathable backsheet consisting of a vapor pervious, relatively liquid impervious outer sheet and a liquid impervious inner panel. The inner panel is placed between the outer sheet and an absorbent core (pad) in the crotch region. In the embodiment shown in FIGS. 1, 4 and 5 the inner panel 24 is of smaller longitudinal dimension than the outer sheet 25 and is positioned only in the crotch area with the absorbent pad 24 overlapping each longitudinal end section. In the embodiment illustrated in FIGS. 2 and 6, the inner panel 24 is of essentially the same dimensions as the outer liquid impervious sheet, the crotch portion of the inner panel, 28, being liquid impervious and the outer or longitudinal end sections 26, 27 on either side of the crotch section 28 being vapor permeable.

As a further illustration of the latter, mention may be made of U.S. Pat. No. 3,881,489 teaching a breathable backsheet comprising a first layer which is a low void volume perforated thermoplastic film and a second layer which is a porous high void volume hydrophobic tissue.

While not intended to be an search of the patent literature, the following additional patents further illustrate the state of the art pertaining to breathable back sheets: U.S. Pat. Nos. 4,425,128 of Motomura; 4,713,068 of Wang et al.; 4,758,239 of Yeo et al.; 4,777,073 issued to Sheth; 4,818,600 and 4,828,556 issued to Braun et al.; and 4,829,096 of Kitamura et al.

In general the prior concepts for providing both breathability and liquid impermeability suffer from one or more of the following deficiencies: (1) can't provide optimum breathability without sacrifice of the critical requirement for liquid-impermeability to prevent escape of body waste through the back of the diaper; and/or (2) inability to prevent edge leakage through the side edges of the crotch area to soil the leg, clothing, bedsheet and/or other surrounding articles.

With respect to the latter, the prior art, as exemplified by the patent literature, also discloses the separate concept of providing barrier strips and the like along the edges to prevent this edge leakage. Illustrative patents providing such means for preventing edge leakage include U.S. Pat. Nos. 3,349,769 issued to Piekarski; 3,572,342 of Lindquist et al.; 4,610,682 of Kopp; and 4,804,379 of Toth et al.

Stated simply, the task of this invention is to provide a disposable diaper providing optimum breathability while at the same time preventing edge leakage, the diaper being characterized further as being of an elegant and cost-effective design which permits the use of less expensive materials in the manufacture of the back sheet.

BRIEF DESCRIPTION OF THE INVENTION

In accordance with this invention, the task is solved by providing a unitary or one piece disposable diaper of per se known configuration, e.g. substantially rectangular or of the hourglass configuration, comprising a back sheet having a crotch portion and corner or wing portions surrounding the crotch portion, the crotch portion having a liquid-impermeable sheet material carrying an absorbent pad of like dimensions for receiving and retaining body waste material, the side edges of the liquid-impermeable sheet material extending around the side edges of the pad and preferably being sealed over the opposed (front) surface thereof, whereby to prevent body waste material from escaping through the back of the diaper or leaking through the side edges, at least the major portion of the surface area of the back sheet surrounding the crotch area containing the liquid-imprermeable sheet material and absorbent pad being liquid-permeable and possessing optimum breathability.

In the preferred embodiment, the back sheet comprises an outer sheet which is of relatively high vapor and liquid permeability and the liquid-impermeable sheet material is sealed to the outer sheet in the crotch portion, the periphery of the impermeable sheet material defining the crotch portion of the diaper containing the absorbent pad.

BRIEF DESCRIPTION OF THE DRAWING

FIG. 1 is a top view of the novel diaper of this invention with a section of the top sheet cut away to reveal the underlying elements;

FIG. 2 is an elevational sectional view taken along lines 2,2 in FIG. 1;

FIG. 3 is a similar view taken along lines 3,3; and

FIG. 4 is a similar view taken along lines 4,4.

DETAILED DESCRIPTION OF THE INVENTION

As was heretofore mentioned, the present invention is directed to disposable diapers which provide breathability for added comfort to the wearer while at the same time providing the requisite protection against escape of body waste materials from within the diaper.

The invention may best be understood by reference to the accompanying illustrative drawing taken in conjunction with the following detailed description.

As shown in the drawing, diaper 10 has its periphery defined by a breathable back sheet 12 having opposed side edges 14,16 and a pair of end edges 18 and 20 connecting the side edges.

The diaper has a crotch portion 22, i.e. a portion adapted to engage the crotch area of the wearer to capture body waste material. While not essential to the practice of this invention, the diaper 10 is shown to have cut-out portions 24 on either side cf the crotch portion so that the diaper is of generally hourglass configuration having four wings or ear portions 26 in the areas surrounding the crotch portion where the end edges connect with the side edges. When the diaper is folded medially to be put on the body, wings 26 engage the waist and stomach areas. It will of course be appreciated that the configuration shown in the drawing for purposes of illustration is not critical and other shapes or configurations will be a matter of individual choice within the expected judgment of the skilled worker.

Secured in fluidtight communication with the back sheet 12 in the crotch portion 22 is a liquid-impermeable sheet material dam or barrier 28 having side edges 30 and 32 and end edges 34 and 36 connecting the side edges.

Seated on the inner surface of dam 28 is absorbent pad 38 for capturing and retaining body waste material. As seen, the side edges 30,32 of dam 28 extend around and over the side edges of pad 38 In this manner, edge leakage of body waste from the pad is precluded.

Preferably, a front or cover sheet 40 (shown partially broken away in FIG. 1 to reveal the underlying elements of the diaper) is also provided. Cover sheet 40, which is liquid-permeable, is shown to be of substantially the same configuration and dimensions as back sheet 12 and the respective sheets are secured together at least around their common periphery. Preferably, the side edges 30, 32 of dam 28 are sealed to the contiguous or back surface of cover sheet 40 to assure a fluid-tight barrier against edge leakage from the absorbent pad, e.g. by heat sealing or by means of a pressure-sensitive adhesive. Alternately, they may be sealed directly to the front surface of the absorbent pad or indirectly through intermediate strips of sheet material adhered to the side edges of the absorbent pad.

A pair of elastic strips 42 are preferably provided on opposed side edges of dam 28 in order to gather the crotch area 22.

A pair of conventional tape fasteners 44 in the waist area permit releasably securing or refastening the opposed end edges 18,20 together around the waist when the diaper is folded to engage the front and back of the body.

When a diaper of the foregoing general description is intended for infants, it may, for example, be on the order of from about 10" to about 25" in length and from about 10" to about 17" at its widest width, in which case the absorbent pad seated on dam 38 and sealed thereto along the side edges may be on the order of from about 8" to about 23" in length and from about 5" to about 12" in width. On the other hand, diapers intended for incontinent adults will of course be substantially larger. For example, the adult diaper may be on the order of from about 26" to about 50" in length and from about 18" to about 40" in width with pad 38 covering the crotch area on the order of from about 24" to about 48" in length and about 5" to about 20" in width.

Breathable back sheet 12, which may be on the order of 0.1 to 1.5 mils thick, may if desired comprise a flexible plastic such as a polyolefin, e.g. polyethylene or polypropylene, a polyester such as polyethylene terephthalate, a cellulose ester such as cellulose acetate or triacetate, etc. which has been perforated to provide the desired air transmission rate or breathability.

However, it will be noted that such plastic materials, are relatively expensive. For instance, the cost of polyethylene, the impermeable polymer conventionally employed for back sheets, has skyrocketed in the past few years.

Since the back sheet 12 need not be liquid-impermeable in accordance with this invention, it will be appreciated that the breathable materials for providing sheet 12 will preferably comprise less expensive materials having the requisite dry strength. By way of illustration, mention may be made of highly porous nonwoven fabrics, paper-based porous materials which, optionally, have been chemically treated for increased structural stability against tearing, porous biodegradable materials, etc.

Dam 28, which also may be on the order of from about 0.1 to about 1.5 mils thick, may comprise any of the impermeable materials heretofore used for back sheets, polyethylene or polypropylene being illustrative.

Pad 38 may comprise any of the absorbent materials heretofore employed in the diaper art, e.g. wood pulp or fluff, cellulose wadding, absorbent cotton fibers, polyester or polyolefin and the like, including mixtures thereof. As is known in the disposable diaper art, one or more layers containing a superabsorbent material may also be utilized.

Permeable top sheet 40 likewise may comprise any of the materials heretofore employed for top sheets, e.g. spun bonded polyester or polypropylene fibers, various nonwoven fabrics, gauze, etc. having the requisite wet and dry strength.

Tape fasteners 44, which per se comprise no part of this invention, may be any of the known tape structures utilizing so-called refastenable pressure-sensitive adhesive, e.g. acrylic adhesive formulations or elastomeric adhesive formulations such as those of the KRATON series (trademark of Shell Chemical Company) which are styrene-isoprene block copolymers.

Elastic strips such as strips 42 are also well known in the diaper art. They may comprise any elastomer such as natural, butyl or synthetic rubber having the requisite tensile force to provide gather, e.g. 100 grams when stretched 100% from the relaxed condition. While shown in the illustrative drawing to comprise a single strand, a plurality of such strands are also contemplate.

In foregoing description, back sheet 12 has been shown to be a continuous film to which dam 28 is sealed in the crotch area.

However, it will be appreciated that the portion in juxtaposition with the major portion of dam 28 is superfluous and may accordingly be eliminated.

It is therefore contemplated that in lieu of the continuous surface area film, the backing may have a central opening or window in the crotch area with the dam 28 sealed around the periphery over the window. In this context, it will of course be appreciated that the dimensions of the window should be slightly smaller than those of of dam 28, e.g. on the order of at least one inch in both length and width, thus leaving a border or peripheral edge of the window of, say, at least 0.5 inch to which the back of dam 28 may be sealed, for example, by heat sealing.

An important feature of the present invention is the fact that the absorbent pad covers only the surface of the liquid-impermeable dam 28, as distinguished from those diapers of the prior art wherein the absorbent pad extends near the edges of the back sheet. Dam 28 prevents escape of body waste materials through the back and edges of the diaper, thereby permitting those areas of the back sheet surrounding the crotch area containing the pad to possess optimum breathability for the comfort of the wearer.

While cover sheet 40 is shown to be of substantially the same configuration and dimensions as the back sheet, it is to be understood that it may only cover the absorbent pad, in which event it will be sealed around its periphery to the periphery of dam 28 and/or to the back sheet just beyond the dam. In this alternate embodiment, breathability of the back sheet will not be compromised by the presence of a superposed cover sheet.

From the foregoing description, it will be seen that the present invention provides an elegant design of simplified construction wherein body waste materials are effectively confined within the crotch area by means of dam 28, thereby permitting the wings surrounding the crotch area to be highly breathable without concern over the possibility of soiling by escape of body waste materials from within the diaper.

It will further be observed that the present invention makes it plausible to obtain a very substantial savings in terms of reduced amounts of polyolefin heretofore customarily employed in back sheet manufacture.

Since certain changes may be made without departing from the scope of the invention herein contemplated, it is to be understood that the foregoing description and accompanying drawing shall be taken as illustrative and not in a limiting sense.

What is claimed is:

1. A breathable unitary disposable diaper adapted when worn to engage the waist and stomach areas of the wearer comprising in order:
   (1) a back sheet having opposed side edges and opposed end edges connecting the side edges, the back sheet defining the shape and dimensions of the diaper, the diaper having a crotch portion adapted to engage the crotch of the wearer to capture and retain body waste material when the diaper is folded medially and worn engaging the waist and stomach areas, the back sheet having peripheral portions defining an opening in the crotch area, at least the major surface area of the back sheet surrounding the opening being liquid permeable and further being characterized as being breathable for the comfort of the wearer;
   (2) a liquid-impermeable sheet material having opposed side edges and opposed end edges connecting the side edges, the sheet material being of substantially the same dimensions as the crotch portion, the liquid-impermeable sheet material being of slightly larger dimensions than the opening in the back sheet and being sealed around its periphery in fluid-tight relationship to peripheral edges of the back sheet surrounding the opening in the back sheet; and
   (3) an absorbent pad adapted for receiving body waste material seated on the free surface of the liquid-impermeable sheet material opposed from the back sheet, the absorbent pad having opposed side and end edges and being of substantially the same dimensions as the sheet material, the sheet material extending around and over the side edges of the pad, whereby the liquid-impermeable sheet material provides a barrier preventing body waste material from escaping through the back of the diaper or through the side edges of the pad.

2. A breathable disposable diaper as defined in claim 1 wherein said breathable portions of said back sheet are further characterized as possessing optimum breathability.

3. A breathable disposable diaper as defined in claim 1 including a liquid-permeable cover sheet covering at least the surface of said pad seated in said crotch area.

4. A disposable diaper as defined in claim 3 wherein said sides of said liquid-impermeable back sheet extending over said pad are secured to the inner surface of said cover sheet.

5. A disposable diaper as defined in claim 3 wherein said cover sheet is of substantially the same dimensions as said back sheet, said back and cover sheets being secured together around their common periphery.

6. A disposable diaper as defined in claim 3 wherein said cover sheet is of smaller dimensions than said back sheet, said cover sheet being secured around its periphery to at least one of said back sheet and said liquid-impermeable sheet material.

7. A disposable diaper as defined in claim 1 wherein said back sheet has cut-out portions on either side of said crotch portion, whereby said back sheet is characterized as being of a generally hourglass configuration.

8. A disposable diaper as defined in claim 1 wherein said back sheet comprises a substantially liquid-impermeable material and said breathable areas are provided by perforations.

9. A disposable diaper as defined in claim 9 wherein said plastic is selected from the group consisting of polyolefins, polyesters and cellulose ester.

10. A disposable diaper as defined in claim 1 wherein said back sheet comprises an initially highly porous material.

11. A disposable diaper as defined in claim 26 wherein said highly porous material is selected from the group consisting of nonwoven fabrics, paper-based porous materials and porous biodegradable materials.

12. A disposable diaper as defined in claim 1 wherein said absorbent pad contains a superabsorbent material.

13. A disposable diaper as defined in claim 1 wherein said back sheet comprises a continuous surface area sheet material.

* * * * *